United States Patent [19]

Veenstra

[11] Patent Number: Plant 7,630

[45] Date of Patent: Aug. 27, 1991

[54] LILY PLANT NAMED PICTURESQUE

[75] Inventor: Rien Veenstra, Wilsonville, Oreg.

[73] Assignee: Oregon Bulb Farms, Inc., Aurora, Oreg.

[21] Appl. No.: 513,483

[22] Filed: Apr. 23, 1990

[51] Int. Cl.[5] ..... A01H 5/00

[52] U.S. Cl. ..... Plt./68

[58] Field of Search ..... Plt./87.4, 68

[56] References Cited

U.S. PATENT DOCUMENTS

P.P. 6,206 6/1988 McRae ..... Plt. 68

*Primary Examiner*—Howard J. Locker

*Attorney, Agent, or Firm*—Charles W. Rummler

[57] ABSTRACT

A new and distinct variety of Asiatic hybrid lily variety of the chalice type particularly distinguished by its profuse production of very large flowers having a yellow orange coloration in a raceme orientation at the upper end of a tall, erect and stately stem having a height of about 120 cm., this plant blooming annually and profusely during mid-season, the plant having a vigorous and very strong growth habit with abundant foliage.

1 Drawing Sheet

BACKGROUND OF THE NEW PLANT

This new Asiatic hybrid lily plant originated as a hybrid seedling produced at Sandy, Oreg. by a cross of an unnamed and unpatented variety selected from my collection of lily plants maintained for breeding purposes with the pollen of a variety identified in my collection as number 28-79 and the present seedling was selected by me for propagation because of its generally yellow orange flower coloration borne at the top of a strong, upright stem of ample height and bearing abundant foliage. Propagation of this selected seedling was carried on under my direction at Sandy, Oreg. by both scaling and tissue culture procedures with such success that propagation in the same manner was continued through several successive generations which demonstrated conclusively that the novel features of the selected seedling would hold true from generation to generation and appeared to be firmly fixed. This particular variety of Asiatic hybrid lily is now being propagated by tissue culture and scaling at Aurora, Oreg.

DESCRIPTION OF THE DRAWING

This new variety of lily plant is illustrated by the accompanying full color photographic drawing, the color rendition being as nearly true to that herein specified as can be reasonably obtained by conventional photographic procedures.

DESCRIPTION OF THE NEW PLANT

The following is a detailed description of my new Asiatic hybrid lily as observed at Aurora, Oreg., with color designations herein stated being according to the R.H.S. Color Chart published by The Royal Horticultural Society of London, England.

THE PLANT

Origin: Seedling.

Parentage:

*Seed parent.*—A hybrid resulting from Lilium Halloween by Lilium Enchantment by Lilium Connecticut King.

*Pollen parent.*—Variety Number 28-79, an unpatented selection from the collection of Lilium plants for breeding purposes at Sandy, Oreg.

Classification:

*Botanic.*—Division — 1A, UPR Asiatic hybrid lily.

*Commercial.*—Hybrid Lilium clone.

Form: An erect, stately single stem.

Height: About 120 cm.

Main stem length: About 120 cm.

Growth: Vigorous, upright and very strong.

Foliage:

*Quantity.*—Abundant.

*Size of leaf.*—About 8 to 14 cm. long and about 1.5 to 2 cm. wide.

*Shape of leaf.*—Linear with entire margins.

*Texture.*—Leathery.

*Aspect.*—Glossy.

*Color.*—Upper side — Dark Green. Under side — A somewhat lighter Green.

Bulbs:

*Size.*—Ranging to 25 cm. in circumference for commercial use.

*Color.*—White.

THE BUD

Shape: Long ovoid with obtuse apex.

Size: Large.

*Diameter.*—About 2.5 cm.

*Length.*—About 8 cm.

Rate of opening: This bud opens slowly at maturity in response to light.

Color:

*When tepals first divide.*—Yellow 14-B.

*When tepals begin to unfurl.*—Yellow 12-A.

Peduncle:

*Length.*—About 30 cm.

*Character.*—Strong and erect.

*Color.*—Yellow Green 146-A.

THE FLOWER

Blooming habit: Once annually and profusely at mid-season.

Size of flower: Very large.

*Diameter.*—About 16 cm.

*Depth.*—About 6.5 cm.

Borne: In a raceme arrangement at the upper portion of a tall, strong stem.

Shape:

*When bloom first opens.*—Cup shaped.

*When bloom matures.*—The flower tends to flatten.

Tepalage:

*Number.*—Six.

*Arrangement.*—Hexagonally with the inner tepals in alternate arrangement above the outer tepals.

*Texture.*—Leathery.

*Aspect.*—Satiny.

*Color.*—Outer tepals — body, Yellow Orange 15-A with Green 143-B at the base. Reverse side — Yellow Orange 14-A. Inside tepals — body, Yellow Orange 14-A with Green 143-B at the base. Reverse side — Yellow 13-B. Each tepal is marked with a greyed-red 185-A brush mark beginning at the top of the nectary and extending for about half of the tepal length with a width of about 1.5 cm. In addition, a small number of greyed-red 185-A elongated spots are present on each side of the nectary below the brush marks.

Pedicel:

*Length.*—About 8 to 10 cm.

*Color.*—Yellow Green 146-A.

*Character.*—Upright, ascending to about 45° above horizontal, and very sturdy.

Discoloration after full bloom: There is very little color change as the flower ages.

Persistance: The tepals stays on the stem approximately three weeks.

Fragrance: None.

Disease resistance: Resistant of fusarium and virus tolerant as observed at Aurora, Oreg.

Lasting Quality: Long, both on the plant and as a cut flower.

THE REPRODUCTIVE ORGANS

Stamens:

*Number.*—Six.

*Arrangement.*—Typical of genus Lilium.

*Anthers.*—Size: About 2 cm. Color: Yellow Green 150-B.

*Filaments.*—Length: About 4 cm. Color: Yellow 9-C.

*Pollen.*—Color: Anthers do not become fully dehiscent and pollen is only occasionally visible — Yellow 7-C.

Pistils:

*Number.*—1.

*Style.*—Length: About 4.5 cm. Color: Green Yellow 1-A.

*Stigma.*—Color: Yellow Orange 17-B.

Character of Ovaries: Typical of the genus Lilium.

FRUIT

Fertility: The fruit may be fertile.

Shape: Ovoid.

Color at Maturity: Soft Brown.

This new variety most nearly resembles the variety Impact (U.S. Plant Pat. No. 5,952). This new variety is yellow in comparison to the range of Impact. It is also male sterile. The stems are very strong with thick, healthy foliage.

I claim:

1. A new and distinct variety of Asiatic hybrid lily plant, substantially as herein shown and described, characterized by its profuse production of relatively large yellow orange flowers the tepals of which are marked with a greyed-red brush mark extending from the top of the nectary for about half of the tepal length, the plant blooming annually in mid-season with a vigorous growth habit and abundant foliage.

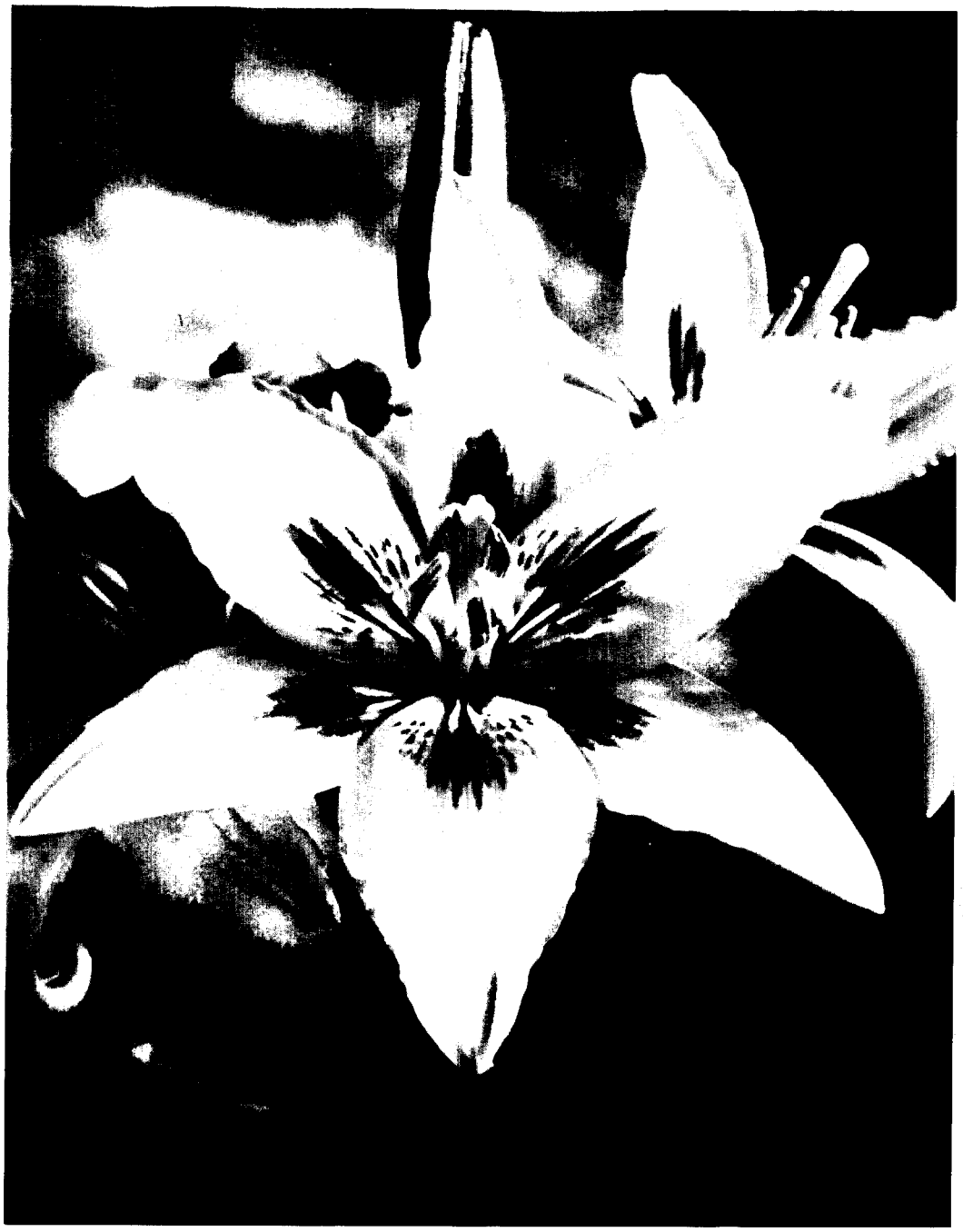

* * * * *